(12) United States Patent
Lipshaw et al.

(10) Patent No.: US 12,115,126 B2
(45) Date of Patent: Oct. 15, 2024

(54) COMPRESSION GARMENTS FOR A LIMB OF A PERSON AND METHOD FOR DONNING THEM

(71) Applicant: MEDI USA, L.P., Whitsett, NC (US)

(72) Inventors: Moses Lipshaw, Hillsborough, NC (US); Jody Erickson, Hillsborough, NC (US); Genesis Cruz-Molina, Winston-Salem, NC (US); Thomas Wright, Raleigh, NC (US)

(73) Assignee: MEDI USA, L.P.

( * ) Notice: Subject to any disclaimer, the term of this patent is extended or adjusted under 35 U.S.C. 154(b) by 350 days.

(21) Appl. No.: 17/192,503

(22) Filed: Mar. 4, 2021

(65) Prior Publication Data

US 2021/0275394 A1    Sep. 9, 2021

(30) Foreign Application Priority Data

Mar. 5, 2020    (EP) .................................... 20161205

(51) Int. Cl.
*A61H 39/04*    (2006.01)

(52) U.S. Cl.
CPC ..... *A61H 39/04* (2013.01); *A61H 2201/0107* (2013.01); *A61H 2201/1638* (2013.01);
(Continued)

(58) Field of Classification Search
CPC .... A61B 17/1325; A61H 1/006; A61H 1/008; A61H 2205/12; A61H 39/04; A61H 2201/0107; A61H 2201/1638; A61H 2201/1642; A61H 2201/1647; A61H 2201/165; A61H 2201/5058; A61H 2201/5061; A61H 2205/065; A61H 2205/125; A61H 2201/0157; A61H 2201/0192; A61H 2201/5071;
(Continued)

(56) References Cited

U.S. PATENT DOCUMENTS 1,443,844 A    1/1923    Jensen
1,495,925 A  *  5/1924    Quertermous .......... A41F 9/007
                                                       24/182

(Continued)

FOREIGN PATENT DOCUMENTS

EP      3103424 A1     12/2016
JP   2015171597 A  *  10/2015 ......... A61F 13/0273
(Continued)

*Primary Examiner* — Mohamed G Gabr
*Assistant Examiner* — Osama Nemer
(74) *Attorney, Agent, or Firm* — Rimon Law

(57) ABSTRACT

Compression garment (1) for a limb of a person, comprising a flexible body portion (2) having a first, limbward side (3) and a second side (4) opposing the first side (3), and at least one band (6) extending from a lateral side (30) of the body portion (2) for wrapping around the limb, wherein the band (6) comprises a fastener (13) such that the end of the band (6) is removably attachable onto the compression garment (1) when wrapped around the limb, whereby the body portion (2) further comprises at least one guiding element (10) providing a channel (9) for receiving the band (6) and guiding the band (6) back over itself when the band (6) spans over the first side (3) to provide an opening (8) for receiving the limb.

20 Claims, 7 Drawing Sheets

(52) U.S. Cl.
CPC ............ *A61H 2201/1642* (2013.01); *A61H 2201/1647* (2013.01); *A61H 2201/165* (2013.01); *A61H 2201/5058* (2013.01); *A61H 2201/5061* (2013.01); *A61H 2205/065* (2013.01); *A61H 2205/125* (2013.01)

(58) Field of Classification Search
CPC .... A61H 2209/00; A61H 39/02; A61H 11/00; A61H 2011/005; A61H 39/00; A61F 5/028; A61F 5/30; A61F 5/0111; A61F 5/0118; A61F 5/0127; A61F 5/013; A61F 13/064; A44B 11/04
See application file for complete search history.

(56) References Cited

U.S. PATENT DOCUMENTS

| | | | | |
|---|---|---|---|---|
| 3,945,046 | A * | 3/1976 | Stromgren | A61F 13/062 |
| | | | | 2/24 |
| 5,451,234 | A * | 9/1995 | Wassermann | A61B 17/1327 |
| | | | | 606/203 |
| 5,989,204 | A | 11/1999 | Lina | |
| 8,491,514 | B2 * | 7/2013 | Creighton | A61F 13/10 |
| | | | | 602/63 |
| 9,474,332 | B1 * | 10/2016 | Naranjo | A44B 11/02 |
| 9,681,991 | B1 | 6/2017 | Warren | |
| 9,795,171 | B2 * | 10/2017 | Lipshaw | A61F 13/085 |
| 10,123,592 | B2 * | 11/2018 | Raymond | F41C 23/02 |
| 10,307,281 | B2 * | 6/2019 | Sorg | A61F 5/01 |
| 2007/0167892 | A1 | 7/2007 | Gramza et al. | |
| 2010/0179586 | A1 * | 7/2010 | Ward | A61B 17/135 |
| | | | | 606/202 |
| 2011/0087145 | A1 | 4/2011 | Farrow et al. | |
| 2013/0085428 | A1 * | 4/2013 | Deshpande | A61H 9/0092 |
| | | | | 601/148 |
| 2015/0230552 | A1 * | 8/2015 | Metcalf | A41B 11/007 |
| | | | | 2/239 |
| 2016/0030267 | A1 * | 2/2016 | Lipshaw | A61H 1/008 |
| | | | | 601/84 |
| 2016/0058623 | A1 * | 3/2016 | Lipshaw | A61F 13/085 |
| | | | | 602/75 |
| 2016/0081836 | A1 * | 3/2016 | Sawle | A41B 11/007 |
| | | | | 2/239 |
| 2017/0273851 | A1 * | 9/2017 | Larmer | A61F 13/08 |
| 2017/0354544 | A1 * | 12/2017 | Lipshaw | A61F 13/104 |
| 2018/0221213 | A1 * | 8/2018 | Hitschmann | A61F 13/085 |
| 2019/0015261 | A1 * | 1/2019 | Lipshaw | A61F 13/085 |
| 2020/0288791 | A1 * | 9/2020 | Breitwieser | A41C 3/0057 |

FOREIGN PATENT DOCUMENTS

| | | | | |
|---|---|---|---|---|
| KR | 101660317 | * | 9/2016 | ......... A61F 13/0273 |
| WO | 0108618 | A1 | 2/2001 | |
| WO | WO-2013138394 | A1 * | 9/2013 | ............. A41B 11/00 |
| WO | WO-2018005955 | A1 * | 1/2018 | ............. A41B 11/00 |

* cited by examiner

COMPRESSION GARMENTS FOR A LIMB OF A PERSON AND METHOD FOR DONNING THEM

CROSS-REFERENCE TO RELATED APPLICATIONS

This application claims priority to European Patent Application serial no. 20 161 205.8 filed Mar. 5, 2020, the contents of which is incorporated herein by reference in its entirety as if set forth verbatim.

BACKGROUND

Field of the Invention

The invention concerns a compression garment for a limb of a person, comprising a flexible body portion having a first, limbward side and a second side opposing the first side, and at least one band extending from a lateral side of the body portion for wrapping around the limb, wherein the band comprises a fastener such that the end of the band is removably attachable onto the compression garment when wrapped around the limb. The invention further concerns a method for donning such a compression garment.

Compression garments for limbs of a person are generally known in the state of the art. Such compression garments have multiple applications, for example therapeutical applications, prophylactic applications and the like. They are also used to improve the general well-being of healthy persons. Compression garments usually comprise a body portion for at least partly wrapping around a limb and one or more bands for wrapping around the limb, in particular together with the body portion, for fastening the compression garment to the limb. Compression exerted onto the limb may, for example, be adjusted using the one or more bands.

However, an effect of the compression garment, be it a therapeutical effect or simply an improvement of the general well-being of a healthy person, sometimes depends on the correct use and placement of the bands. Since bands are usually elongate structures having a length which may even exceed the circumference of the limb, correct manual placement of the bands may be complicated, in particular leading to oblique positioning and/or confusion regarding fastening positions for the bands.

Regarding applications of compression garments, massage, acupressure, and reflexology treatments are well-accepted examples of a pressure treatment, which may be used for therapy as well as the improvement of the general well-being of healthy persons. For example, these treatments may be applied to relieve symptoms such as pain and stress. Usually, such pressure treatments require active physical energy input from a practitioner or are self-administered by the person seeking relief from symptoms or a general improvement of the well-being. Given the strenuous physical exertion required to deliver these treatments, many types of massage devices have been developed to reduce the burden of therapy, or, in general, treatment.

Examples for actively powered pressure treatment devices include massage chairs, leg and foot massagers, vibrators, vibrating pads, inflatable pressure cuffs, and similar devices that require an electrical energy source. Examples for passive pressure treatment devices include rollers, foam mats, support pads, and similar devices that either require the user to continually exert energy to deliver effective pressure or to bear weight on the device to receive counter pressure through gravity.

WO 2017/165678 A1 discloses a compression garment for neurological and circulatory disorders, which includes a body portion and a pad. The body portion may be operable to wrap around a foot and the pad can be attached to an inner surface of the body portion. The pad can include an outward protrusion and/or an inward recess, wherein the pad is applied to exert pressure on the abductor hallucis and flexor hallucis *brevis* muscles of the foot. That is, this device has in particular been specifically designed to provide pressure to predetermined, concrete anatomical features, in this example in particular for the treatment of the restless leg syndrome. Applying pressure to the abductor hallucis and flexor hallucis *brevis* muscles on the bottom and medial side of the foot helps alleviate the impulses and urges to move the legs while at rest.

While this exemplary device also uses tensioning bands, it is directed to only the treatment of defined anatomical features of the foot and does not provide adjustability, additionally suffering from the drawbacks regarding usage of bands laid out above.

It is thus an object of the current invention to provide a pressure garment providing improved handling of the bands, in particular regarding accurate placement and comfort, while still providing adjustability and, in particular, also various adjustments regarding the application area and type.

This object is achieved by providing a compression garment. Advantageous embodiments are described in the dependent claims.

SUMMARY OF THE INVENTION

In a compression garment for a limb of a person according to the current invention, the compression garment comprising a flexible body portion having a first, limbward side and a second side opposing the first side, and at least one band extending from the lateral side of the body portion for wrapping around the limb, wherein the limb comprises a fastener such that the end of the band is removably attachable onto the compression garment when wrapped around the limb, the body portion further comprises at least one guiding element providing a channel for receiving the band and guiding the band back over itself when the band spans over the first side to provide an opening for receiving the limb.

In particular, using the fastener, the band may be attached onto itself, while, in embodiments, it may also be possible to attach the band to the body portion. Preferably, the band may be optionally attached to one of itself and the body portion. If the band is fastenable on itself, the band may be guided back onto itself using the guiding element.

When the compression garment according to the invention is in use, the band extends from one lateral side of the body portion, in particular a lateral side edge, spans over the first side to the opposing lateral side to create the opening and is guided through the channel back over itself for fastening the end to the outside of the garment, in particular the band itself and/or the body portion. In this context, extending from a lateral side edge means that the band is fastened or fixed to the body portion at or near the lateral side edge.

The invention thus proposes a unique closure system, where the at least one band is fed through a channel to guide the tensioning, direction, and placement of the at least one band. In this manner, for example, the person may pull the band fed through the channel of the guiding element to adjust tension without the risk of displacing the band, in particular misplacing it such that a treatment effect is mitigated or even negated.

The choice of fastening position on the garment, in particular on the band itself, determines pressure exerted by the band and also the body portion, since, after wrapping around the limb/creating the opening for the limb, the band is again guided, using the guiding element, over a defined area of the body portion, providing compression there. Preferably, the channel is provided at the second side of the body portion, as is the guide element.

In a particularly preferred embodiment, the length of the band is dimensioned such that, for a defined limb circumference range, the band, in use, completely circumnavigates the limb and thus the remaining garment including the body portion, such that the tension distribution around the whole compression garment, is improved and, due to guidance through the channel, also locally clearly defined.

In preferred embodiments, the compression garment may be a wrap, which is donned by wrapping the compression garment around the limb. However, the current invention may also be applied to non-wrap garments, like, for example, compression stockings and the like, where accurate placement, uniform distribution of compression and easy handling for bands can be achieved.

The invention is especially advantageously applicable to applications where local pressure treatment is to be applied, for example when using body portions not completely wrapping around the limb for a treatment of arms, legs, hands and/or feet. In particularly preferred embodiments, the body portion may be configured to press a pad or the like onto certain predefined areas of the limb, as further explained below.

It can generally be said that, in particular for a wrap as compression garment, the body portion and the band may together wrap around the limb when in use.

Preferably, the fastener comprises a hook-and-loop fastener. Hook-and-loop fasteners are particularly preferred, since many, in particular textile, materials have been developed and proposed which may be used as a loop portion, to which the hook portion of the fastener may engage. In particular, the bands and/or the body portion may comprise on their outer surface a material comprising loops suitable for engagement with the hook portion of the fastener. In this manner, the hook portion, which is preferably provided at the end of the band, may be attached anywhere onto the band and/or the body portion where the material, in particular the loop material, is present. In preferred embodiments, velour may be used as loop material.

Thus, in preferred embodiments, the body portion and/or the at least one band may comprise a cushioning layer and/or structural layer, in particular a velour layer. Of course, also other types of composite materials for the body portion and/or the bands are conceivable.

Alternatives for using a hook-and-loop fastener in the current invention comprise snap fasteners, magnetic fasteners, latches and the like, but are less preferred.

The at least one band and/or the body portion may be at least partly inelastic and/or at least partly elastic, but are usually both flexible. At least section-wise provided elasticity of the band and/or the body portion, may, in particular be provided to implement a compression measurement system, as will be further described below.

In embodiments, the at least one band and/or the body portion may be trimmable, in particular to customize the garment to a specific limb of a person. For example, the at least one band may be trimmable to be able to shorten the band for smaller circumferences and the like, where it is preferred to have the hook portion of a hook-and-loop fastener removably attachable to the end of the band. Of course, it is also possible to have a trimmable body portion, for example, if the concrete treatment requires smaller areas to be covered, or the like. To facilitate trimming of the at least one band and/or the body portion, indicia may be provided on the at least one band and/or the body portion, for example marking trimming lines for certain circumferences of the limb and/or modes of treatment.

It is generally noted that the guiding element is preferably positioned and/or formed on the second side of the body portion, such that the end of the band extending from the lateral side naturally juts out of the channel on the outer side of its beginning, and not on its limbward side.

In especially preferred embodiments, the guiding element is elongate and/or at least one guiding sleeve, and/or the channel is segmented, wherein the guiding element comprises multiple guiding segments, in particular belt loops. If the guiding element is a guiding sleeve, the guiding sleeve may extend in a longitudinal direction, corresponding to the longitudinal direction of the channel, and may have openings in peripheral directions, in particular having a partial sleeve design with periodically repeated peripheral openings. However, it is also possible to use, for example, equally spaced belt loops which are pointwise or sectionwise defining the channel. In both cases, advantageously, the band is guided over a greater longitudinal extent, thus providing improved and robust guidance on the body portion, in particular the second side of the body portion.

A guiding sleeve, however, may of course also be continuous, that is, without peripheral openings, which is in particular preferred if the guiding sleeve is to be manufactured from a one-piece basic element with the body portion, for example, by folding a section of the basic element over itself to form the channel and thus the guiding element.

Also, generally and preferably, the guiding element and/or the at least one band are formed integrally with the body portion. In particular, the body portion and the band and/or the guiding element can be formed from one piece. Preferably, however, the bands are attached to a one-piece element for the body portion and the guiding element to improve material yield in production. For example, the combined body portion-guiding element piece and the bands may be cut separately from a basic material, whereafter the bands may be sewed to the other piece to obtain a basic element from which the compression garment can be formed.

In preferred embodiments, the guiding element may comprise a folded-over section of the body portion fastened back onto the body portion to form the channel. For example, a one-piece element for forming the body portion and two guiding elements may have double the size of the body portion to be formed such that two opposing sections of the one-piece element may be folded over to meet in the middle, where they are sewed onto the lower section of the one-piece element, which forms the body portion, such that the two guiding elements, each defining a separate channel, are created.

Preferably, the body portion may be three-dimensionally pre-shaped to conform to the limb, in particular by using darts, for example diamond darts. In concrete embodiments, the body portion may be laterally raised to provide a seating for the limb. In such an embodiment, the body portion does not fully wrap around the limb, but only partially, in particular around less than 50% of the limb. For example, the at least one lateral side edge from which the at least one band extends and its opposing lateral side edge may be raised.

This indicates correct positioning for the limb and thus guides the person to correct donning of the compression garment. The limb may be inserted in its longitudinal direction between the raised lateral side edges into the opening for receiving the limb.

In a concrete, preferred embodiment, the body portion, two bands and two guiding elements can be formed from one basic element by sewing. The basic element may be one piece, i.e. have the bands integrally formed, or may have the bands sewed to it. The basic element comprises a central area designed to form the body portion, wherein the central area comprises two diamond darts adjacent to the lateral side edges, wherein the portions at the outer side of the diamond are not connected, such that two diamond wings are formed for each diamond dart. The bands are formed at or attached to diagonally opposite diamond wings, such that, when the diamond darts are sewed together, the bands extend from the so-formed lateral side edges of the so-formed body portion, in particular perpendicularly, wherein the lateral side edges are preferably slightly raised to conform to the shape of the limb. The basic element further comprises two side flaps or side sections along the sides perpendicular to the lateral side edges, wherein the flaps can be folded to the second side of the so-formed body portion to create the channels for the bands and thus the guiding elements, which are preferably guiding sleeves. Preferably, both flaps may be attached in the middle of the central portion in one seam to provide both guiding elements.

In an especially preferred embodiment, the compression garment may comprise multiple bands extending laterally from the body portion to wrap around the limb, wherein a channel for each band is provided by the at least one guiding element, in particular and preferably a separate channel for each band. In this manner, bands can be provided across multiple sections of the body portion and/or the limb. For each of these bands, compression may be separately adjustable in a simple, guided and efficient manner. Providing separate channels for each band provides accurate guidance for each of these bands and thus for the whole donning process.

Preferably, for at least one pair of bands, the bands extend from opposing lateral sides, in particular lateral side edges, of the body portion to wrap around the limb side-by-side. In this manner, opposingly oriented bands may be used which, however, are parallel and adjacent in use. Such an opposing band design provides tensioning balance and helps prevent the compression garment, in particular in case of a wrap, from migrating in one specific direction of applied tension.

In preferred embodiments, at least one of the at least one band and/or the body portion may comprise a measuring system, in particular for measuring elongation and/or tension, and/or for determining a compression level applied to the limb by the garment. Using such a measuring system further simplifies purposefully choosing a specific compression. For example, the measuring system may use indicia positioned on an elastic section of the body portion and/or at least one of the at least one band and an associated measurement device, such that the distance between the indicia can be measured. Hence, an elongation and/or tension is measured, which may then be correlated to a certain compression level. Such compression level measuring systems may, for example, be termed built-in pressure system (BPS). Of course, other types of measuring systems known from the art may also be employed, for example those using attachable indicia and/or magnetic interactions. In any case, preferably, a compression level applied to the limb is determined as a result of the measurement.

In especially preferred embodiments, the compression garment further comprises a pad, in particular an acupressure pad, to exert pressure to the limb under the first side of the body portion. Such a pad may have a characteristic shape to exert pressure on specific anatomical features, for example muscles. The pad is placed under the first side under the body portion in use, such that it is pressed against the limb by the first side of the body portion.

Preferably, the pad is a multi-dimensional topographical pad that provides areas of high and low pressure. In this manner, a certain, predefined pressure distribution can be achieved. In concrete, preferred embodiments, the pad may have at least one outward protrusion on its limbward surface, wherein the protrusion may have a T-shape and/or the protrusion may be dimensioned and/or positioned to contact predetermined regions of the limb in a given orientation of the pad. In other words, the topography may be chosen such that, due to the protrusions, higher pressure is exerted to certain anatomical features, while lower pressure is applied in other regions. A T-shape has been shown to be particularly advantageous for the foot, where, in different orientations, as further described below, different anatomical features may be pressurized, leading to an individually customizable acupressure effect.

Thus, it is generally preferred that the pad is an acupressure pad. Acupressure is a technique in which physical pressure is applied to acupuncture points, i.e., certain anatomical features, with the aim of providing comfort, in particular clearing blockages and the like.

In concrete embodiments, the pad may comprise a foam base layer and a topography layer having the protrusions. That is, the pad may comprise multiple layers, wherein the topography or, more concretely, the protrusions, are defined by at least one topography layer.

In especially preferred embodiments, the pad may be positionable under the body portion in multiple orientations. In this context, the pad may be held in place by the compressions garment in use, while it is also possible to use means for fastening the pad to or in the body portion.

Preferably, the pad may be removably attachable to the first side of the body portion by a fastening means and/or the body portion may comprise a pocket on its first side for receiving the pad. Preferably, the fastening means may comprise a hook-and-loop fastener for easy attaching and removing, in particular in different orientations.

To facilitate positionability in multiple different orientations, the pad, in particular the acupressure pad, may have the shape of a disk or square.

In such embodiments a topographical and/or geometric pad design, in particular an acupressure pad, is combined with an adjustable wrap such that sustained adjustable passive pressure is applied to acupressure and/or reflexology points on the body while at rest. This completely new approach allows acupressure and/or reflexology treatment, in particular for the foot and the hand, that no longer require the user to continually exert a force or bear weight to sustain the pressure effect. As explained, the pad, in particular the acupressure pad, may be designed to provide acupressure to multiple locations of the limb, while, in the preferred embodiment, the pad is designed to be releasably attached, for example via hook-and-loop fastening means, and be freely rotatable in the compression garment, in this case preferably a wrap. By using a pad geometry further comprising a base layer of foam, the conversion of pressure provided by the body portion into the topography layer of the pad is improved. In summary, a compression garment, in particular a wrap, may be provided which is intended to massage and stimulate acupressure point on a limb, for example the soles of a foot, during periods of rest and relaxation to help relieve tired, achy feet and legs. In particular, stress, pain and anxiety relief, calm feet and legs, improved circulation and improved sleep quality may be provided as benefits. Due to the preferably freely orientable pad, in particular acupressure pad, the person may choose which acupressure points are to be stimulated. If, for example, a T-shaped protrusion is used, four different orientations of the T may be proposed which can be chosen as suitable. Of course, other shapes departing from the T-shape are also envisioned, depending on the limb and the area where the pad shall be applied.

The guiding elements for the bands have proven to be very advantageous in combination with such a pressure pad, in particular acupressure pad, since adjustable, well-placed compression may be easily and intuitively be applied. When using a pair of juxtaposed bands extending from opposing lateral sides, even the risk of unintentional movement of the already positioned pad is minimized. However, it has been shown that a freely orientable acupressure pad itself, even without guiding elements for bands, is already advantageous.

Thus, in a second aspect, the invention also concerns a compression garment for providing acupressure to a limb of a person, comprising
- a flexible body portion having a first, limbward side and a second side opposing the first side,
- at least one band extending from a lateral side of the body portion for wrapping around the limb, wherein each band comprises a fastener such that the end of the band is removably attachable onto the garment when wrapped around the limb, and
- an acupressure pad to exert pressure to the limb under the first side of the body portion, the acupressure pad being positionable in multiple orientations under the first side of the body portion held in place by the compression garment or by a direct fastening means and/or the body portion comprising a pocket at its first side for receiving the pressure pad in multiple orientations.

All remarks regarding the pad analogously apply to this variant of the compression garment.

Thus, an adjustable compression garment, in particular wrap, is provided to deliver passive treatment pressure to relieve stress and pain at the limb. The compression garment, in particular the wrap, having the pad can be configured to target different areas of the limb and/or use different pressure profiles, such that the person may choose orientation of the acupressure pad and compression to feel most comfortable and obtain the best therapeutic treatment effect and/or general improvement of well-being. The compression garment requires only the initial application energy to don the compression garment to provide sustained treatment pressure. It does not require an electrical energy source, gravity, or further energy from the person wearing the compression garment to provide the treatment effect. This allows the person to be at complete rest and, in particular, non-ambulatory while using the compression garment.

As already explained above regarding the first aspect of the invention, it is preferred that the compression garment comprises at least two bands extending from opposing lateral sides of the body portion for wrapping side-by-side around the limb. Tension balance and displacement protection are provided in this manner, as well as, as generally the case when using more than one band, the option of applying locally varied compression, that is, compression profiles.

While it is in principle possible to hold the acupressure pad under the body portion by the compression exerted by the body portion, in preferred embodiments, the acupressure pad may be removably attachable to the first side of the body portion by a fastening means, for example, as already discussed, a hook-and-loop fastening means.

Of course, as laid out above, it is also preferable to provide the guiding elements for the bands to gain the respective advantages. Thus, also for the compression garment of the second aspect, the body portion may further comprise at least one guiding element providing a channel for receiving the band and guiding the band back over the garment, in particular over itself, when the band spans over the first side to provide an opening for receiving the limb. All remarks regarding the guiding element and the compression garment of the first aspect of the invention also apply here, such that the same advantages can be achieved.

In a third aspect, the invention also concerns a method for donning a compression garment of the second aspect of the invention, wherein the acupressure pad is attached to the first side or placed into the pocket in a chosen orientation, and, after or while donning the compression garment, compression is adjusted using the bands. These steps can also characterize a method for providing acupressure to a limb, in particular a foot, of a person using a compression garment according to the second aspect of the invention.

In this manner, general acupressure relief can be provided on the limb in an adjustable manner, since the compression and the choice of acupressure or reflexology points on the limb are both adjustable. Sustained adjustable passive pressure can be applied to acupressure or reflexology points on the body while addressed.

BRIEF DESCRIPTION OF THE DRAWING

Further details and advantages become apparent from the following description of concrete embodiments taken in conjunction with the drawings, in which.

DETAILED DESCRIPTION

Figure 1:
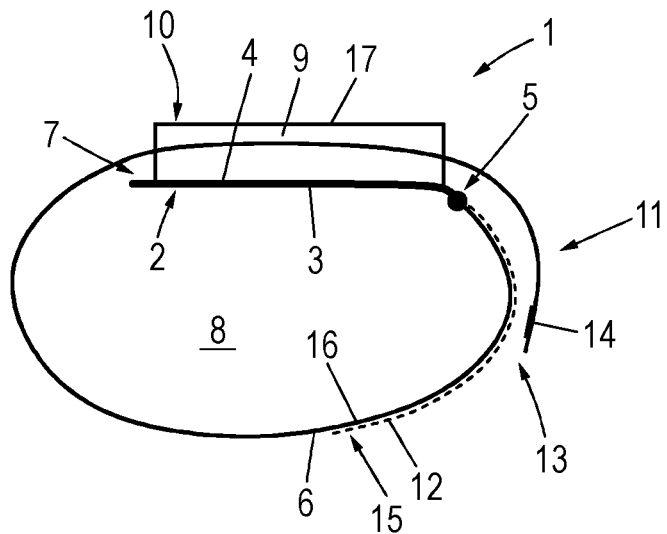
FIG. 1 is a principle drawing of a first, general embodiment of a compression garment according to the current invention.

FIG. 1 is a general principle sectional view of a compression garment 1 according to the present invention, in this case a wrap. The compression garment 1 comprises a body portion 2 having an inner, limbward, first surface 3 and an outer surface 4 opposing the first surface 3. From a lateral side edge 5, a band 6 extends. The band 6 spans over the first surface 3 to the opposite lateral side edge 7 of the body portion 2, thereby creating an opening 8 into which the limb, for example a foot or a hand, can be inserted. At the opposing lateral edge 7, the band 6 is fed into a channel 9 provided by a guiding element 10 on the second side 4 of the body portion 2, through which it is guided back to the lateral side edge 5 from which the band 6 extends such that the end 11 of the band 6 is positioned over itself, as shown in FIG. 1. Since at least the outer side of the band 6 at least partly comprises a loop material 12 acting as the loop portion of a hook-and-loop fastener 13, the hook portion 14 provided at the end 11 of the band 6 allows to attach the band 6 at variable positions onto itself. It is noted that the body portion 2 and/or the guiding element 10 may also have the loop material 12 on their outsides, such that the end 11 of the band 6 can also be attached there.

In this case, the loop material 12 is a velour material, and, at least in the section of the band 6 covered by the loop material 12, the band 6 thus comprises a structural layer 15, namely the loop material 12, and a cushioning layer 16 for comfortable contact with the skin of the person wearing the compression garment 1. The body portion 2 may also have the cushioning layer 16 on its first side 3.

Figure 2:
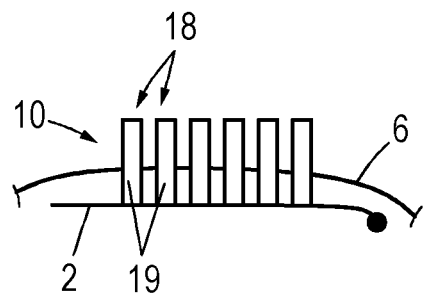
FIG. 2 shows an alternative realization of a guiding element.

In the embodiment shown in FIG. 1, a guiding element 10 is provided as a guiding sleeve 17 extending in a longitudinal direction corresponding to the longitudinal direction of the channel 9, wherein it is continuous peripherisally, that is, comprises no openings. However, the guiding element 10 may also be segmented comprising multiple guide segments 18, as indicated in FIG. 2, wherein the guide segments 18 are formed by belt loops 19.

It is noted that in the embodiment of FIG. 1, the band 6 is fixed to the lateral side edge 5 of the body portion 2 by sewing, however, the band 6 may also be fastened or fixed near the lateral side edge 5, in particular on the second side 4.

In use, the limb extends through the opening 8, such that, by pulling the band end 11, a desired tension level for the band 6 can be chosen. As the band 6 also acts onto the second side of the body portion 2, the body portion 2 is also pressurized against the limb. Multiple bands 6 also allow choosing certain compression profiles along the length of the limb covered by the compression garment 1.

Figure 3:
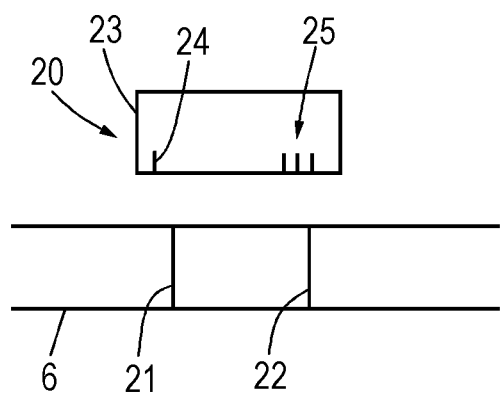
FIG. 3 illustrates an exemplary implementation of a compression measuring system.

FIG. 3 shows an exemplary compression measurement system 20 which may be implemented in the bands 6 or in the body portion 2. For illustrative reasons, in FIG. 3, integration into a band 6 is shown. While the bands 6 and the body portion 2 may be partly or fully inelastic, they may also be partly or fully elastic. FIG. 3 refers to an elastic section of band 6. In this section, two indicia 21, 22 are provided such that the distance between the indicia 21, 22 changes when the tension in the band 6 is increased, i.e. the distance increases when higher tension is applied. The distance between the indicia 21 and 22 can be measured and associated with a compression level or compression range by using a measurement card 23 which has the reference indicium 24 and multiple further indicia 25 associated with different compression levels/compression ranges.

However, it is also possible to apply other types of measurement systems 20 in compression garments 1 according to the invention.

It is noted at this point that the band 6 and the body portion 2 may also be trimmable to customize the compression garment 1. For example, further indicia may be provided associated with certain limb circumferences.

Figure 4:
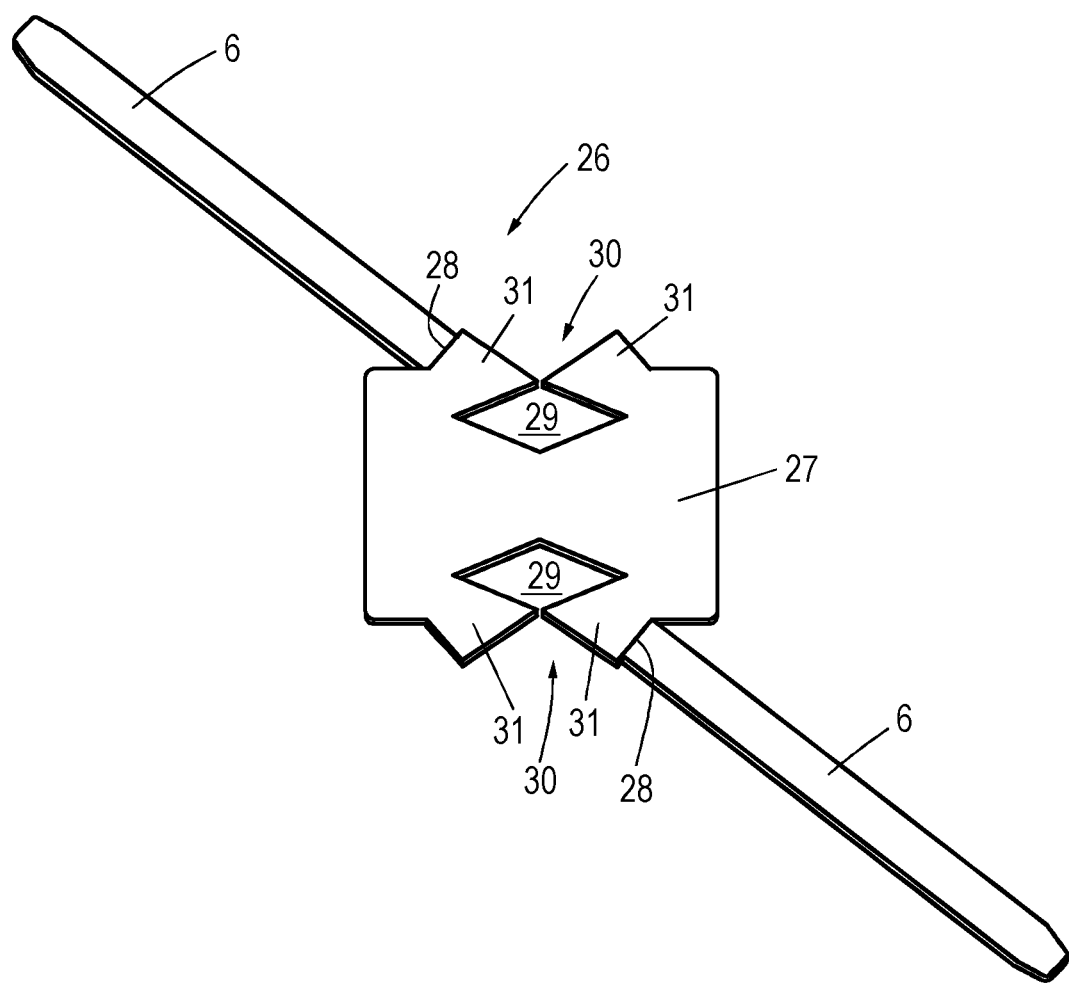
FIG. 4 shows a basic element from which the compression garment according to the current invention can be formed.

FIG. 4 shows a basic element 26, from which the body portion 2, two bands 6 and two guiding elements 10 can be formed. The basic element 26 comprises a one-piece central area 27 from which the body portion 2 and the guiding elements 10 will be formed, while, in this embodiment, the bands 6 have been sewed to the central portion 27 along seams 28. In this manner, a better yield regarding the material of the basic element 26 can be achieved during cutting.

The central area 27 comprises two diamond darts 29 al lateral sides 30 of the central area 27. The portions at the outer side of the diamond darts 29 are not connected and form diamond wings 31, wherein the bands 6 extend from diagonally opposing diamond wings 31.

Figure 5:
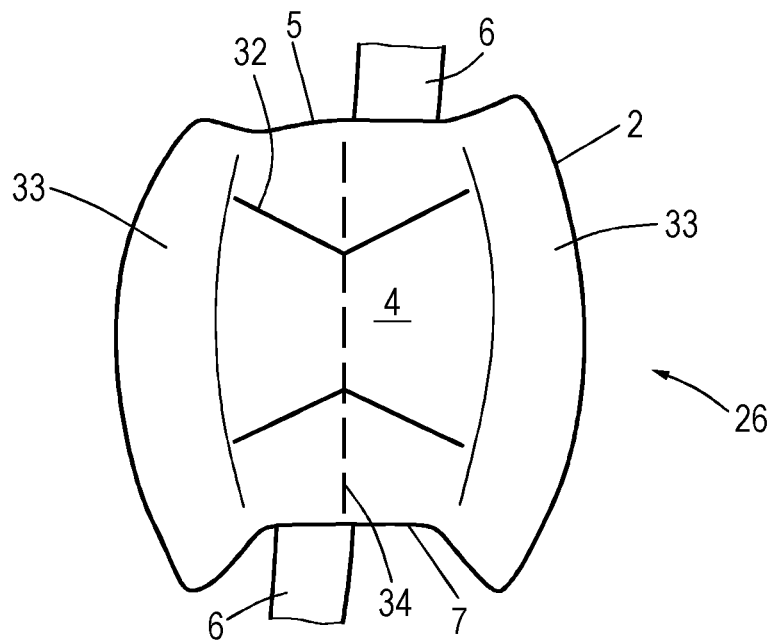
FIG. 5 shows a first step for forming the compression garment.

As shown in FIG. 5, the diamond darts 29 have already been closed by seams 32, such that centrally, the body portion 2 with its second surface 4 is formed. Please note that the bands 6, which are shown clipped for a more compact illustration, extend from opposing lateral side edges 5, 7 in a relatively shifted manner, such that, when the bands 6 span over the first side 3 of the body portion 2, they are parallelly aligned side-by-side.

In the next step, two side flaps 33 are folded inwards back onto the second side 4 of the body portion 2 to meet in the middle at a central seam line 34 already indicated in FIG. 5.

Figure 6:
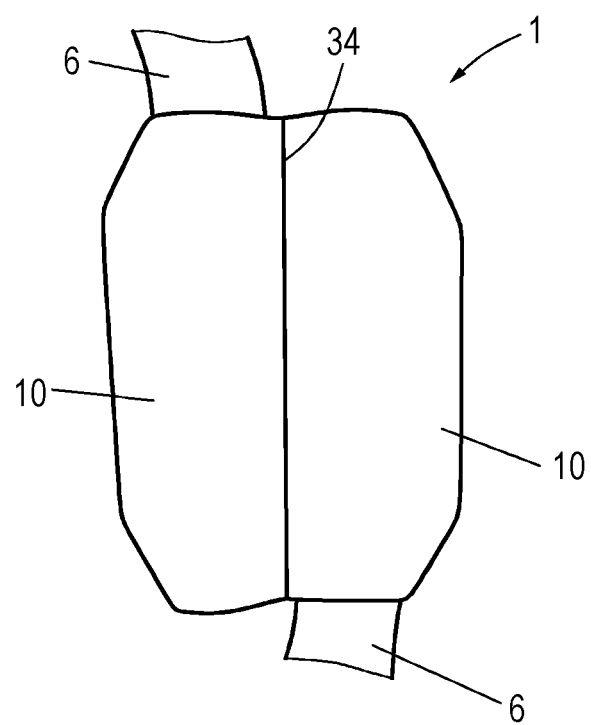
FIG. 6 shows the formed compression garment with loose bands, FIGS. 7-10 explain how the bands are guided through channels of guiding elements.
Figure 7:
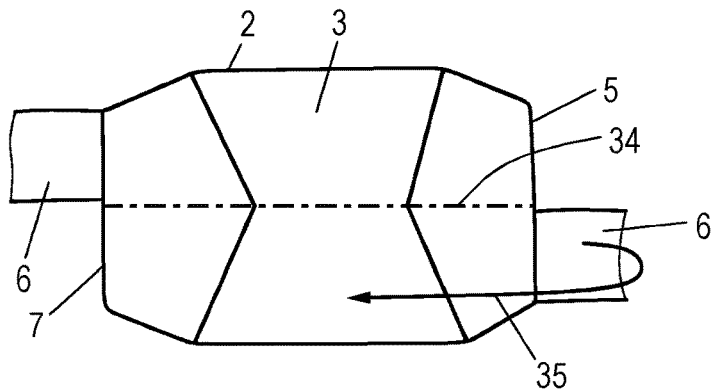
Figure 8:
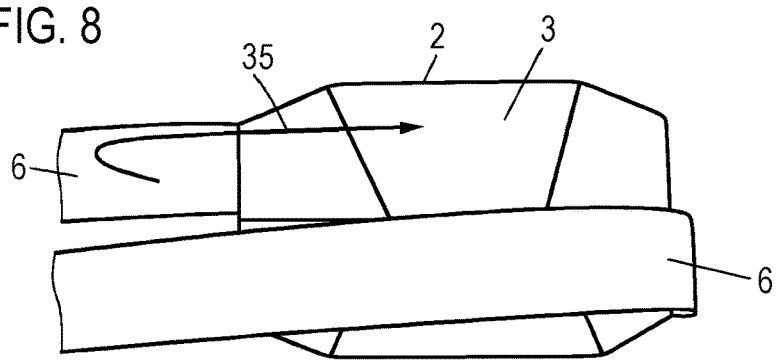
Figure 9:
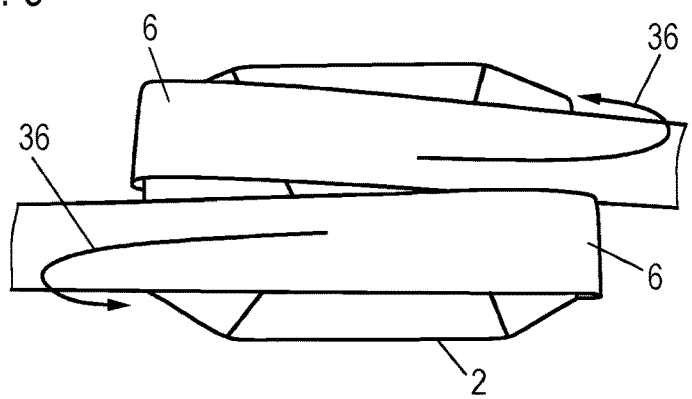

As shown in FIG. 6, both side flaps 33 are sewed to the second surface 34 along the central seam line 34, in particular with a single seam, such that two guiding elements 10, in this case guiding sleeves 17, each defining a channel 9, are formed.

Figure 10:
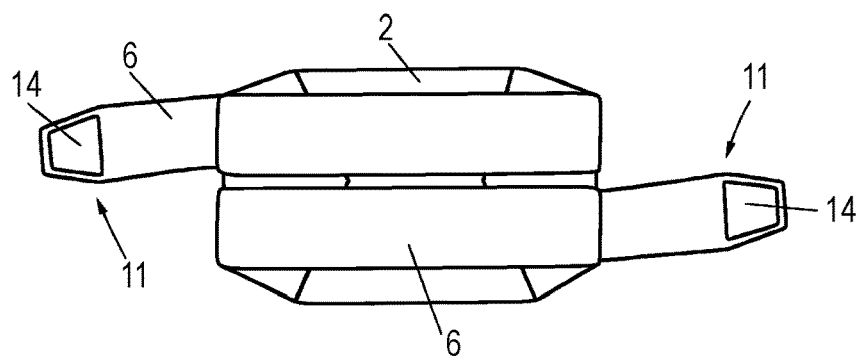

To place the so-formed compression garment 1, still with loose bands 6, into a state ready-to-use, as illustrated in FIGS. 7 to 10, both bands are folded over the first, limbward side 3 of the body portion 2 to the opposing lateral side edge 5, 7 according to arrows 35 and then, see arrow 36, fed back to their original lateral side edges 5, 7 through the channels 9 in guiding elements 10, such that the situation in FIG. 10 arises. The end 11 of the bands 6 are guided back over the beginnings of the respective bands 6, such that they may be fastened onto themselves using the hook portion 14.

Using two opposing bands 6 not only allows to adjust to different tension levels for each of the bands 6, but also provides tensioning balance and helps prevent the compression garment 1 from migrating in one specific direction of applied tension.

As can be seen, the bands 6 completely circumnavigate the compression garment 1 to improve tension distribution throughout the compression garment 1.

Figure 11:
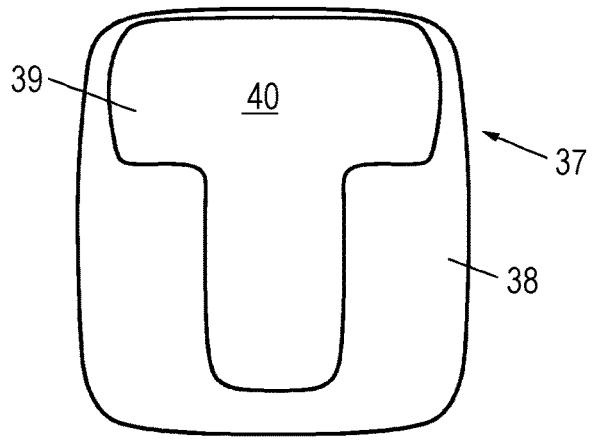
FIG. 11 shows a top view of an acupressure pad usable in compression garments according to the invention.
Figure 12:
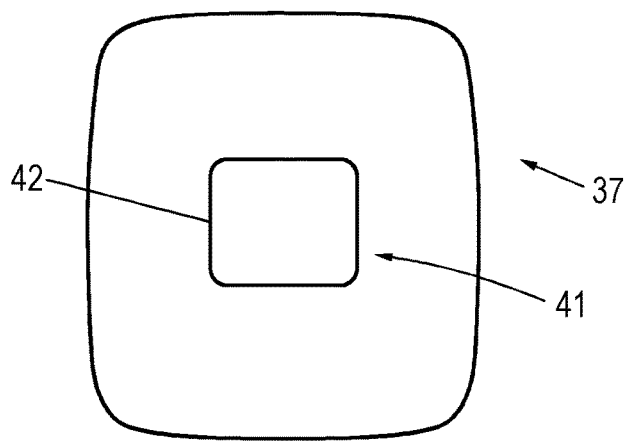
FIG. 12 shows a bottom view of the acupressure pad.

In preferred embodiments, the compression garment 1 additionally comprises an acupressure pad 37 as exemplarily shown in FIGS. 11 and 12, wherein FIG. 11 shows a view of the limbward side, while FIG. 12 shows a view from the opposite side. As can be seen from FIG. 11, the pad 37 comprises a foam layer 38 and a topography layer 39, wherein the topography layer 39 defines an, in this case T-shaped, protrusion 40. Applying the pad 37 to an area of the limb applies higher pressures at anatomical features touched by the protrusion 40 and lower pressures elsewhere. Generally, it can be said that the pad 37 is a multi-dimensional topographical pad 37 that provides areas of high and low pressures.

In this embodiment, the pad 37, see FIG. 12, comprises a fastening means 41, in this case another hook portion 42, to removably attach the pad 37 to the first side 3 of the body portion 2. Obviously, the essentially quadratically shaped pad 37 can be attached to the body portion 2 in multiple different orientations and thus applied to the limb in all those orientations.

Figure 13:
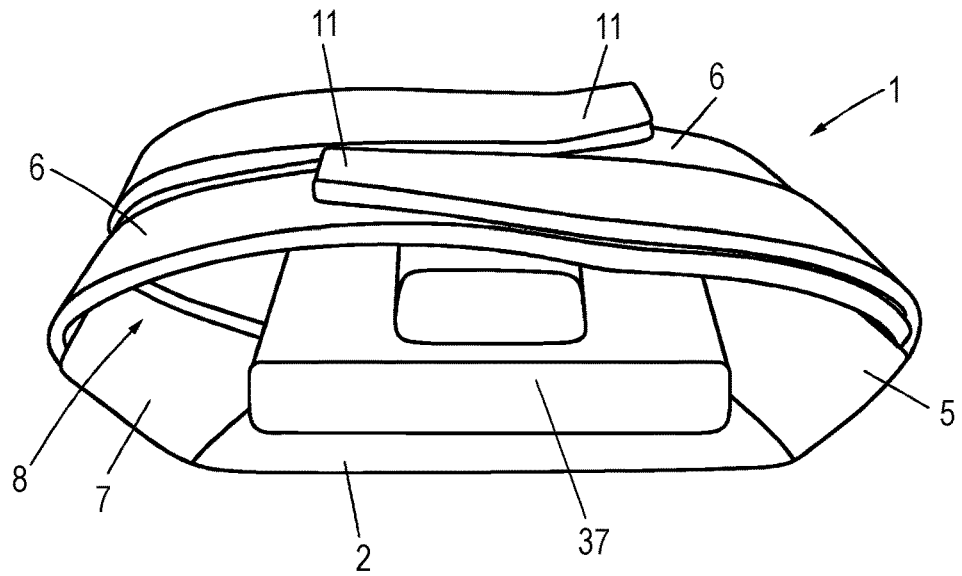
FIG. 13 shows a side view of a compression garment according to the invention including the acupressure pad.
Figure 14:
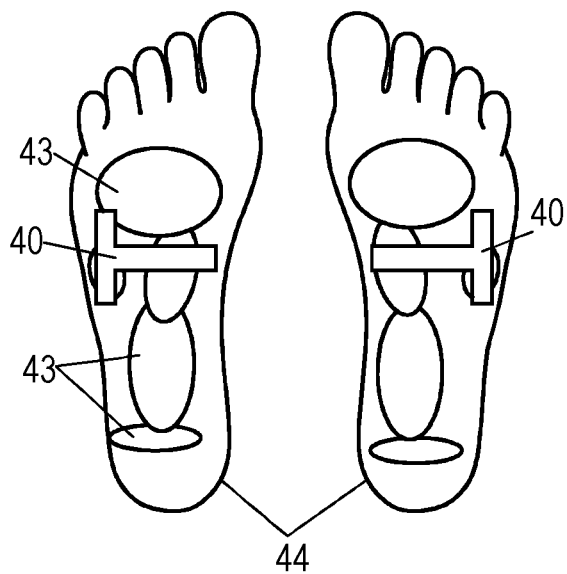
FIGS. 14-17 illustrate pressurized anatomical features in different orientations of the acupressure pad.
Figure 15:
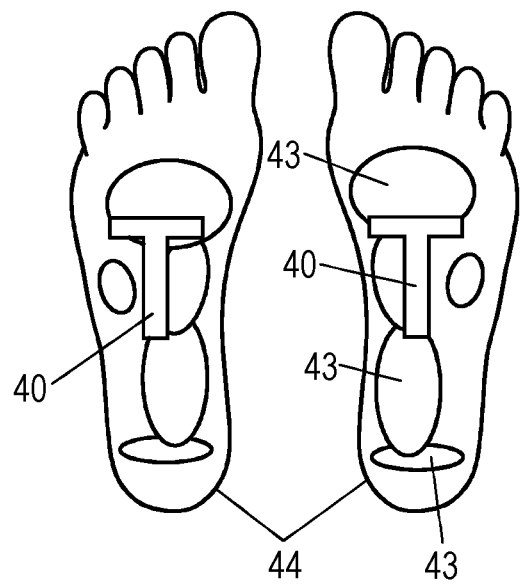
Figure 16:
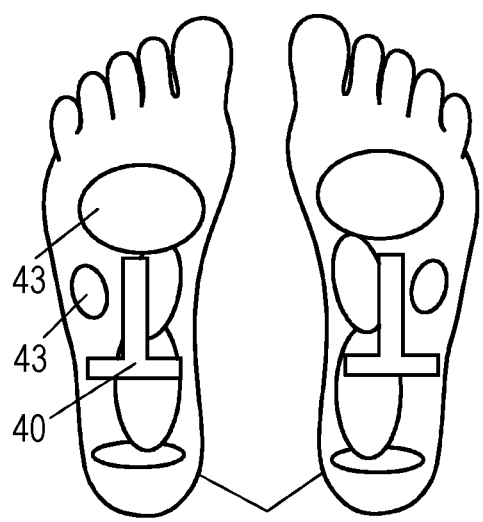
Figure 17:
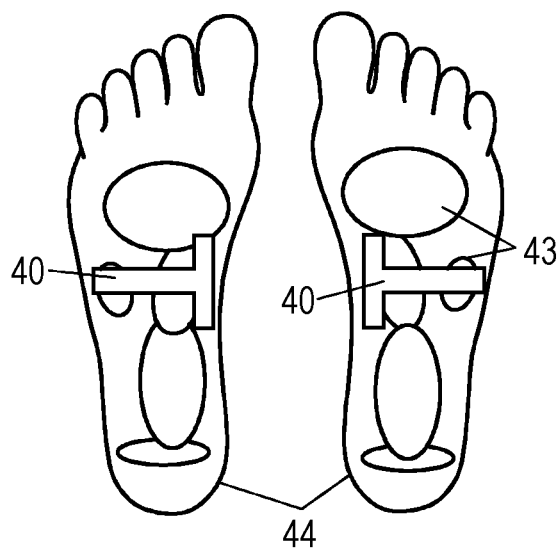

FIG. 13 shows the compression garment 1 with the pad 37 attached to body portion 2, wherein the ends 11 of the bands 6 are attached onto other sections of the bands 6 to minimize the size of opening 8 for transport. Note that the lateral side edges 5, 7 are raised due to the diamond darts, such that the body portion 2 is adjusted to the shape of the limb, in this case, as an example, the foot.

FIGS. 14 to 17 illustrate how different anatomical features 43 of feet 44 are pressurized in different orientations of the protrusion 40. In this manner, adjustable acupressure can be easily provided at adjustable compression levels, leading to symptom relief in therapeutic and further treatment use.

Figure 18:
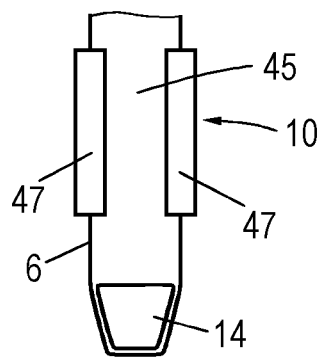
FIG. 18-20 show another alternate realization of a guiding element.
Figure 19:
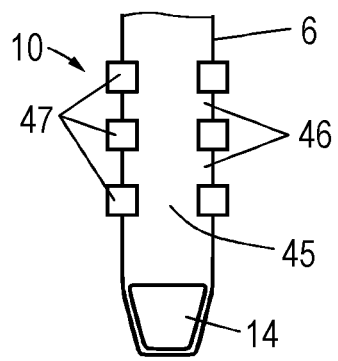
Figure 20:
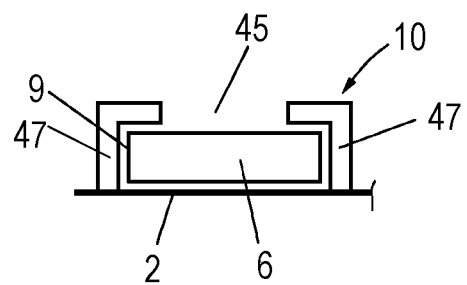

FIGS. 18 to 20 illustrate other alternative realizations for the guiding element 10 in embodiments of the invention, wherein FIGS. 18 and 19 are top views. In the embodiment shown in FIG. 18, the guiding element 10 is centrally split providing an opening 45 extending in the longitudinal direction of channel 9. The embodiment of FIG. 19, which is particularly material-saving, uses separate disconnected belt loops, such that the central opening 45 is flanked by further openings 46 of disconnected belt loops. As shown in FIG. 20, which is a cross-sectional view, the two respective components 47 of the guide element 10 each clasp the band 6 from opposing sides, such that the band 6 is firmly held and the channel 9 is defined.

The invention claimed is:

1. Compression garment (1) for a limb of a person, comprising a flexible body portion (2) having a first, limbward side (3) and a second side (4) opposing the first side (3), and at least two bands (6) extending from a lateral side (30) of the body portion (2) for wrapping around the limb,
wherein each of the at least two bands (6) comprises a fastener (13) such that one end of each of the at least two bands (6) is removably attachable onto the compression garment (1) when wrapped around the limb and the other end of each of the at least two bands is immovably fixed to the lateral side of the body portion, characterized in that the fastener of each of the at least two bands is arranged on an inner side of each of the at least two bands and the corresponding attaching surface is arranged on an outer side of each of the at least two bands to attach each of the at least two bands at variable positions onto itself, and the body portion (2) further comprises at least two guiding elements (10), each of the at least two guiding elements providing a channel (9) for receiving each of the at least two bands (6) and guiding each of the at least two bands (6) to wrap over itself when each of the at least two bands (6) spans over the first side (3) to provide an opening (8) for receiving the limb,
wherein each of the at least two guiding elements (10) is elongate creating one channel (9) or one guiding sleeve (17) disposed on top of the second side (4),
wherein the at least two guiding elements are positioned next to each other along their respective longitudinal sides, and
wherein each of the at least two guiding elements is closed along thea longitudinal direction of the channel.

2. Compression garment (1) according to claim 1, characterized in that the at least two guiding elements (10) and/or the at least two bands (6) are formed integrally with the body portion (2).

3. Compression garment (1) according to claim 1, characterized in that the body portion (2) is laterally raised to provide a seating for the limb.

4. Compression garment (1) according to claim 1, characterized in that the at least two bans comprises multiple bands (6) extending laterally from the body portion (2) to wrap around the limb, wherein a channel (9) for each band (6) of the multiple bands is provided by the at least two guiding elements (10), and wherein a separate channel (9) is provided for each band (6) of the multiple bands.

5. Compression garment (1) according to claim 4, characterized in that for at least one pair of bands of the multiple bands (6), the at least one pair of bands (6) extend from opposing lateral sides (30) of the body portion (2) to wrap around the limb side-by-side.

6. Compression garment (1) according to claim 1, characterized in that at least one of the at least two bands (6) and/or the body portion (2) comprises a measuring system (20) for measuring elongation, tension, and/or for determining a compression level applied to the limb by the garment (1).

7. Compression garment (1) according to claim 1, characterized in that the compression garment (1) further comprises an acupressure pad to exert pressure to the limb under the first side (3) of the body portion (2).

8. Compression garment (1) according to claim 7, characterized in that the pad (37) is removably attachable in multiple orientations, to the first side of the body portion (2) by a fastening means (41), and/or that the body portion (2) comprises a pocket on its first side for receiving the pad (37), in multiple orientations.

9. Compression garment (1) according to claim 8, characterized in that the pad (37) has the shape of a disc or square and/or has at least one outward protrusion of a T-shape on its limbward surface.

10. Compression garment (1) for a limb of a person, comprising a flexible body portion (2) having a first, limbward side (3) and a second side (4) opposing the first side (3), and at least two bands (6) extending from a lateral side (30) of the body portion (2) for wrapping around the limb,
wherein each of the at least two bands (6) comprises a fastener (13) such that an end of each of the at least two bands (6) is removably attachable onto the compression garment (1) when wrapped around the limb and the other end of each of the at least two bands is immovably fixed to the lateral side of the body portion, characterized in that the fastener of each of the at least two bands is arranged on an inner side of each of the at least two bands and the corresponding attaching surface is arranged on an outer side of each of the at least two bands to attach each of the at least two bands at variable positions onto itself, and the body portion (2) further comprises at least two guiding elements (10) disposed on top of the second side (4), each of the at least two guiding elements providing a channel (9) for receiving each of the at least two bands (6) and guiding each of the at least two bands (6) to wrap over itself when each of the at least two bands (6) spans over the first side (3) to provide an opening (8) for receiving the limb,
wherein the at least two guiding elements are positioned next to each other along their respective longitudinal sides, and
wherein the at least two guiding elements (10) comprise a folded-over section (33) of the body portion (2) fastened back onto the second side of the body portion (2) to form the channel (9).

11. Compression garment (1) according to claim 10, characterized in that the at least two bands comprises multiple bands (6) extending laterally from the body portion (2) to wrap around the limb, wherein a channel (9) for each band (6) of the at least two bands is provided by the at least two guiding elements (10), and wherein a separate channel (9) is provided for each band (6) of the at least two bands, the at least two bands (6) extend from opposing lateral sides (30) of the body portion (2) to wrap around the limb side-by-side.

12. Compression garment (1) according to claim 10, characterized in that at least one of the at least two bands (6) and/or the body portion (2) comprises a measuring system (20) for measuring elongation, tension, and/or for determining a compression level applied to the limb by the garment (1).

13. Compression garment (1) according to claim 10, further comprising an acupressure pad to exert pressure to the limb under the first side (3) of the body portion (2).

14. Compression garment (1) according to claim 13, characterized in that the pad (37) is removably attachable in multiple orientations, to the first side of the body portion (2) by a fastening means (41), and/or that the body portion (2) comprises a pocket on its first side for receiving the pad (37) in multiple orientations.

15. Compression garment (1) for a limb of a person, comprising a flexible body portion (2) having a first, limb-ward side (3) and a second side (4) opposing the first side (3), and at least two bands (6) extending from a lateral side (30) of the body portion (2) for wrapping around the limb,
wherein each of the at least two bands (6) comprises a fastener (13) such that an end of each of the at least two bands (6) is removably attachable onto the compression garment (1) when wrapped around the limb and the other end of each of the at least two bands is immovably fixed to the lateral side of the body portion, characterized in that the fastener of each of the at least two bands is arranged on an inner side of each of the at least two bands and the corresponding attaching surface is arranged on an outer side of each of the at least two bands to attach each of the at least two bands at variable positions onto itself, and the body portion (2) further comprises at least two guiding elements (10) disposed on top of the second side (4), each of the at least two guiding elements providing a channel (9) for receiving each of the at least two bands (6) and guiding each of the at least two bands (6) to wrap over itself when each of the at least two bands (6) spans over the first side (3) to provide an opening (8) for receiving the limb,
wherein the at least two guiding elements are positioned next to each other along their respective longitudinal sides, and
wherein the body portion (2) is three-dimensionally pre-shaped to conform to the limb by using one or more darts (29) closed by seams (32).

16. Compression garment (1) according to claim 15, characterized in that each of the at least two guiding elements (10) and/or each of the at least two bands (6) are formed integrally with the body portion (2).

17. Compression garment (1) according to claim 16, characterized in that the body portion (2) is laterally raised to provide a seating for the limb.

18. Compression garment (1) according to claim 17, characterized in that the at least two bands comprises multiple bands (6) extending laterally from the body portion (2) to wrap around the limb, wherein a channel (9) for each band (6) of the at least two bands is provided by the at least two guiding elements (10), and wherein a separate channel (9) is provided for each band (6) of the at least two bands.

19. Compression garment (1) according to claim 18, characterized in that for at least one pair of bands of the at least two bands (6), the at least one pair of bands (6) extend from opposing lateral sides (30) of the body portion (2) to wrap around the limb side-by-side.

20. Compression garment (1) according to claim 15, characterized in that at least one of the at least two bands (6) and/or the body portion (2) comprises a measuring system (20) for measuring elongation, tension, and/or for determining a compression level applied to the limb by the garment (1).

* * * * *